US006955757B1

(12) United States Patent
Maltin

(10) Patent No.: US 6,955,757 B1
(45) Date of Patent: Oct. 18, 2005

(54) APPARATUS FOR PROCESSING FLUIDS

(76) Inventor: Christopher Maltin, Goulds House, Horsington, Somerset BA8 0EW (GB)

( * ) Notice: Subject to any disclaimer, the term of this patent is extended or adjusted under 35 U.S.C. 154(b) by 134 days.

(21) Appl. No.: 10/110,089

(22) PCT Filed: Oct. 12, 2000

(86) PCT No.: PCT/GB00/03920

§ 371 (c)(1),
(2), (4) Date: Apr. 8, 2002

(87) PCT Pub. No.: WO01/27040

PCT Pub. Date: Apr. 19, 2001

(30) Foreign Application Priority Data

Oct. 12, 1999 (GB) .................................. 9924085

(51) Int. Cl.[7] .............................................. C02F 3/00

(52) U.S. Cl. .................. 210/150; 210/151; 210/175; 210/220

(58) Field of Search ....................... 366/101; 261/124; 210/175, 180, 188, 150, 151, 220

(56) References Cited

U.S. PATENT DOCUMENTS

| 3,988,396 A | 10/1976 | Stannard | 261/124 |
| 4,142,975 A | 3/1979 | Kinzer | 210/195 |
| 4,274,838 A * | 6/1981 | Dale et al. | 48/111 |
| 6,109,345 A * | 8/2000 | Giacomel | 165/185 |
| 6,257,751 B1 * | 7/2001 | Maltin | 366/101 |

FOREIGN PATENT DOCUMENTS

| GB | 2 158 840 A | 9/1984 |
| GB | 2 305 369 A | 9/1996 |
| WO | WO 99/67176 | 6/1999 |

* cited by examiner

Primary Examiner—Chester T. Barry
(74) Attorney, Agent, or Firm—Gifford, Krass, Groh, Sprinkle, Anderson & Citkowski, P.C.

(57) ABSTRACT

A treatment system for a process fluid, comprising a plurality of chambers interconnected with one another in sequence such that a process fluid can pass through them, means for determining the process conditions in at least some of the chambers by varying at least one process parameter while the process fluid is resident in the chamber such that different parts of a complex process are encouraged to take place in different chambers of the system.

22 Claims, 5 Drawing Sheets

APPARATUS FOR PROCESSING FLUIDS

The present invention relates generally to apparatus for processing fluids and particularly, although not exclusively, to apparatus for the treatment of slurries comprising solids in liquids.

The present invention provides improved apparatus in which complex treatment processes, particularly biological processes can take place.

One technical field in which such slurries occur is in the treatment of organic material by bacteriological action, especially the so-called slurry digestion processes which are known for the treatment of organic waste materials.

Where bacteriological action is involved, especially one which takes a relatively extended time period for completion, any material which follows a shorter than average route through the process environment may consequently be inadequately treated.

Variations in process results are particularly unacceptable if the treatment process is a biological breakdown of waste products because any partially-treated material may not be suitable for the uses to which the fully-treated material may be put. For example, biological breakdown of organic waste material such as animal excrement produces, when the treatment is complete, a residual solid material which is odour-free and high in nutrients suitable for use as a horticultural or agricultural fertiliser. Inadequately treated material, on the other hand, may not be odour-free, and more importantly may contain residual contaminants, pathogens or seeds the former of which could be dangerous or at least detrimental and the latter of which, if still viable, reduce the value of the material as a fertiliser.

Apparatus of the general type to which the present invention relates is describes in the applicant's earlier British Patent Application No. GB-A-2 305 369.

According to one aspect of the present invention, there is provided a treatment system for a process fluid, comprising a plurality of chambers ($11_1$, $11_2$, $11_3$, $11_4$, $11_5$, $11_6$) interconnected with one another in sequence such that a process fluid can pass through them, and means (19, 20) for introducing a gas into at least some of the said chambers to form bubbles (24, 25) which act to drive circulation of the process fluid within the chamber as the bubbles (24, 25) rise within the process fluid, characterised in that there are further provided heating means (37) for selectively controlling the temperature of the process fluid resident in at least one selected chamber ($11_1$, $11_2$, $11_3$, $11_4$, $11_5$, $11_6$) whereby to encourage different bacteria to colonise different chambers of the system due to the different temperature conditions set up in these chambers.

In another aspect the present invention provides a method of treating a process fluid in a plurality of chambers ($11_1$, $11_2$, $11_3$, $11_4$, $11_5$, $11_6$) interconnected with one another in sequence such that a process fluid can pass through them sequentially, comprising the steps of introducing gas into at least some of the chambers to form bubbles (24, 25) whereby to drive circulation of the process fluid as the bubbles (24, 25) rise within that or those chambers, and withdrawing surplus gas, including gas generated within the chamber by the process taking place therein, characterised in that the temperature of the process fluid within at least some of the chambers is controlled selectively whereby to encourage different parts of a complex process to take place in different chambers of the system due to the different temperature conditions set up in these chambers.

In one embodiment of the present invention apparatus for the treatment of process fluids may be so arranged that the residence time of the fluid within the various chambers of the apparatus can be made at least substantially the same for substantially all parts of the process material. The exceptions to this comprise aggregations or lumps of solid material which cannot pass out of the outlet due to their size, which may reside in the apparatus or in one chamber of the apparatus, for a longer time, until they have been reduced in size by the process, to dimensions such as to allow passage through the outlet, or until separate collection by a solids collection arrangement which will be described in more detail below.

Another problem encountered with the treatment of process fluids lies in the fact that the fluids arriving for treatment may also contain other material, particularly particles of metal, glass, stones and the like. Obviously, such materials are not affected by the bacteriological treatment to which the process fluid is subject, and, if steps are not taken to remove them, can lead to a build up of unwanted solids in the treatment plant and at least a reduction in throughput, with possibly a clogging or blockage of the entire system.

In another embodiment of the present invention there are provided means by which such inorganic solids (or indeed, organic solids where these are sufficiently dense or aggregated in sufficiently large particles such as not to be broken down by the bacteriological process in the residence time of the material within the treatment apparatus) may be removed from the treatment apparatus for further processing prior to separate treatment, recycling, or (as appropriate) reintroduction to the treatment apparatus.

In another embodiment of the invention there is provided treatment apparatus in which a chamber for receiving a treatment fluid has at least two unobstructed interior regions in each of which the process fluid is caused to follow a circulating path, the chamber being so formed that the paths followed by the process fluid between an inlet and an outlet to the chamber are not substantially different in length for all parts of the process fluid.

In a preferred embodiment of the invention the bubble inlets are arranged in a plurality of rows thereof whereby to provide a "curtain" of bubbles. In a configuration such as that outlined above, in which the chamber has two regions in which the process fluid is caused to circulate in opposite directions, and in which the transfer of the process fluid from one to the other takes place in its transit through the chamber, the circulation-driving bubbles may form a "curtain" between the two regions such that the process fluid must pass across the curtain of bubbles in its transit through the chamber. Any relatively dense particle of solid material entrained with the process fluid will, on passing through the bubble curtain, experience a significant reduction in its buoyancy thereby falling to the solids-collection region.

A configuration in which two rows of bubble inlets are provided may have a channel between the two rows of bubble inlets serving as this collection region, and such channel may house an auger or other means for driving the solid particles collecting therein towards a distribution point from which they can be removed from the vessel.

Removal of such solids from the vessel may involve the use of a water column within which the solids may be elevated, for example by means of a further auger or a gas lift apparatus, and which serves to maintain the gas tight closure of the vessel while nevertheless allowing solids to be extracted therefrom.

Regardless of the form of the chambers (and certain preferred configurations will be described hereinafter in more detail) a treatment system for a process fluid may comprise a plurality of vessels in sequence defining the chambers with means for varying the process parameters, so that different processes take place in different vessels. There may further be provided means for directing process fluid from the outlet of a chamber to an inlet of the same chamber or to an inlet of another chamber upstream or downstream in relation to the flow of process fluid through the system.

Other parameters than the temperature may also be controlled within the chambers, including the rate of flow of process fluid through the chamber, the precise bacteriological content of the chamber (in the case of biological processes, which may be achieved by introducing particular bacteria into it for inoculating the material therein) and/or the introduction or presence of other process reagents, in particular liquids or gases.

The introduction of a gas into the treatment vessel may be undertaken simply to drive the circulation of the process fluid within the vessel, in which case the gas may be chosen as one contributing to the maintenance of aerobic or anaerobic conditions as the case may require, or alternatively the gas may be one which takes part in the reaction proceeding within the vessel.

Whether the plurality of chambers are formed as compartments within a vessel by partitioning, or whether they are formed as separate vessels interconnected by ducting, it is preferred that at least some of the walls defining the chamber are in contact with a heat exchange fluid which may be driven in counter current with respect to the direction of flow of process fluid through the system. In this way, for example, exothermic reactions taking place in some of the chambers can be cooled by the heat exchange fluid and the heat transferred to other chambers whereby to raise the temperature of the material therein.

Various embodiments of the present invention will now be more particularly described, by way of example, with reference to the accompanying drawings, in which.

Figure 1:
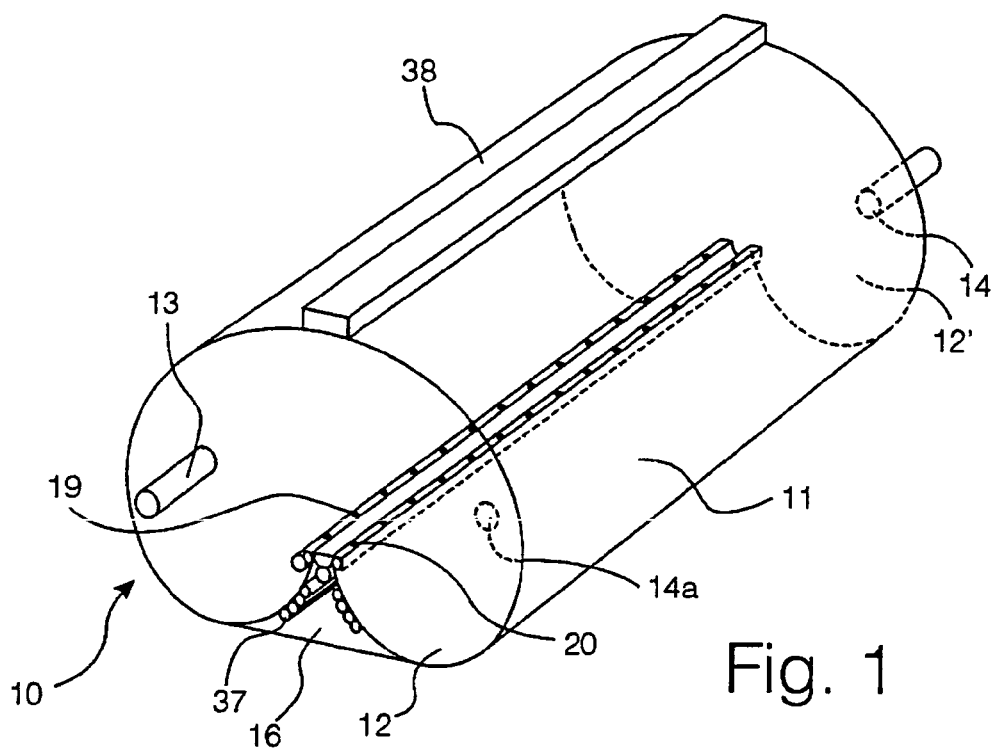
FIG. 1 is a perspective view of a vessel formed as a first embodiment of the invention.

Referring now to FIG. 1, the embodiment illustrated comprises a single vessel is in the form of an elongate tank of cardioid type cross section as described in more detail in the applicant's earlier published GB Patent Application referred to above. The vessel 11 has an end wall 12 with an inlet duct 13, and an opposite end wall 12' with an outlet duct 14.

The cross sectional shape of the vessel 11 (as illustrated more clearly in FIG. 2) gives rise to two separate regions or chambers generally indicated 17, 18 separated by a central median plane of symmetry X—X (FIG. 2) on either side of which are located elongated gas delivery pipes 19, 20 having rows of holes 21, 22 from which, in use, two rows of bubbles 24, 25 (FIG. 2) rise to form a "curtain" of bubbles. The inlet duct 13 at one end of the vessel 11 opens into a first region or chamber 17, on one side of the curtain of bubbles 24, 25 and the outlet duct 14 leads from the other region or chamber 18, so that process material introduced into the vessel 11 is caused to circulate first in one direction (anticlockwise as shown in FIG. 2 by broken line arrows A) as it passes along the first region and is caused to transit from one region or chamber 17 to the other region or chamber 18 across the curtain of bubbles 24, 25 where it circulates in the opposite direction (clockwise as viewed in FIG. 2) as it passes through this region before exiting from the vessel 11 through the outlet 14.

In its passage across the curtain of bubbles 24, 25 any heavy particles of dense material entrained with the process fluid experience significantly less buoyancy, due to the presence of the bubbles, than they experience within the regions 17, 18, resulting in these particles falling into a collection channel 26 located between the two rows of openings 21, 22 from which the introduced gas flows.

Figure 2:
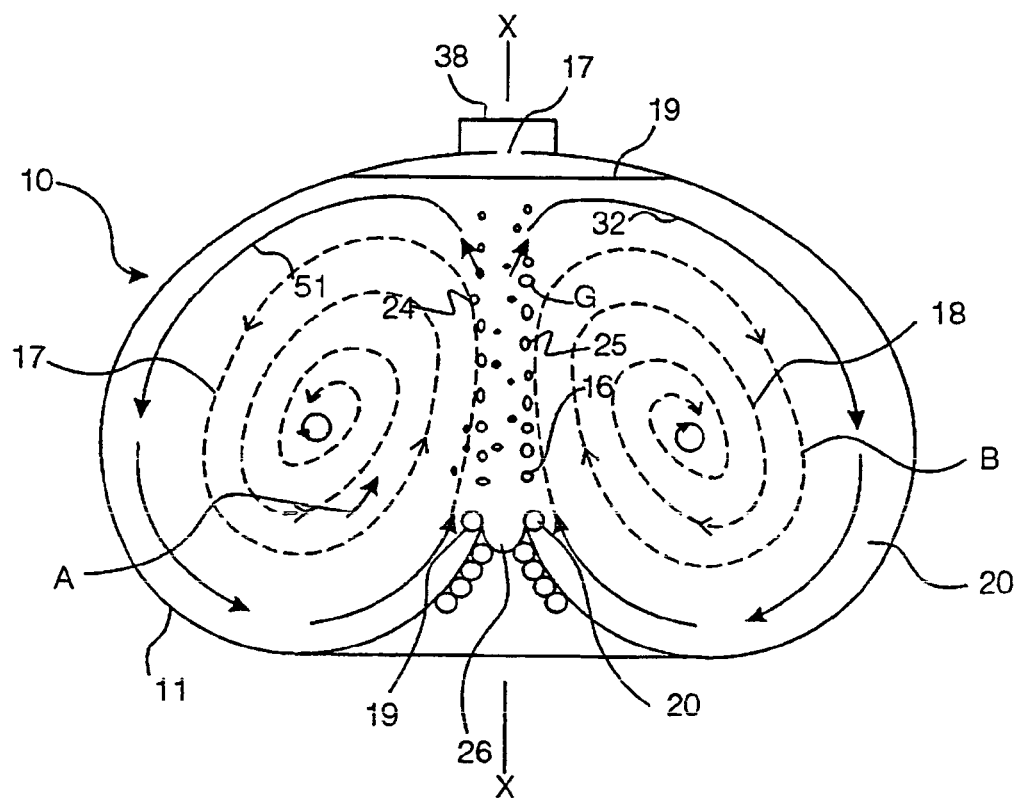
FIG. 2 is a sectional view through the embodiment of FIG. 1.

In its circulating flow within the region 17 the process fluid follows a spiral path gradually increasing in diameter as it travels along the length of the vessel 10, and conversely within the region 18 it follows a spiral path of gradually decreasing diameter as represented by the broken line arrows B in FIG. 2. The actual path followed by an individual particle, therefore in its spiral flow around the region or chamber 17, gradually increasing in diameter and travelling along the length of the chamber 10, (and the corresponding circulating path around and along the region or chamber 18) extends for a distance many times greater than the length of the vessel 10. This extended circulating path means that the residence time of each particle is always at least a minimum value represented by the transit time along one of the regions 17, 18. In fact the residence time for each particle is substantially the same as that of all the other particles because there is no alternative route by which a particle may inadvertently pass from the inlet duct 13 to the outlet duct 14 along a path less than that travelled by the other particles thereby receiving less treatment within the vessel. For example, if a particle remains within the region 17 while travelling along the entirety of its length before crossing to region 18 it will be located at the outlet end and pass relatively quickly to the outlet 14. Another particle may circulate to a radially outer position in the region 17 quickly and pass across the curtain into region 18 while still close to the inlet end. This particle now has to travel the full length of the vessel before reaching the outlet 14 following a spiral path which has substantially the same length as the path followed by the particle first described.

Figure 5:
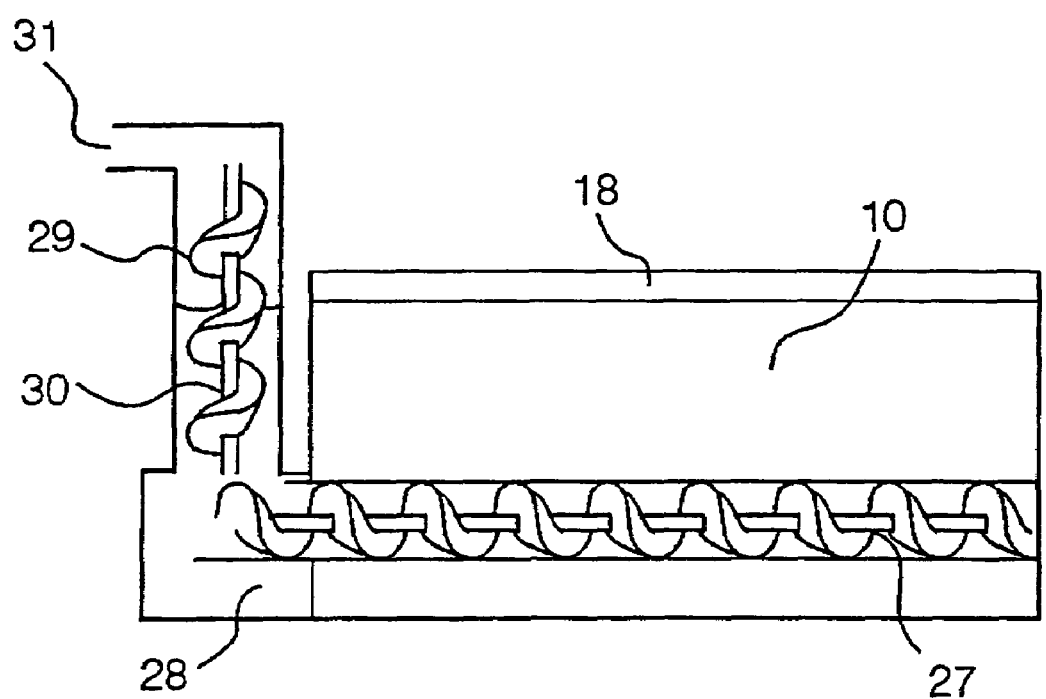
FIG. 5 is a side view of a vessel formed as a further embodiment of the present invention.

The collection channel 26 for heavy particles houses an auger 27, as illustrated schematically in FIG. 5, which exits into a closed chamber 28 from which extends an upright column 29, filled with the process liquid. This column 29 houses a vertical auger 30 leading to an outlet 31. Particles collecting in the channel 26 are thus conveyed first to chamber 28 and then out along the column 29 rising above the surface of the treatment fluid and leaving through the exit 31 from where they may be segregated; those particles which may be treated by the process (for example dense lumps of organic material) may be broken down and reintroduced into the process fluid, while those which cannot be processed with this treatment are recycled to other uses.

Figure 3:
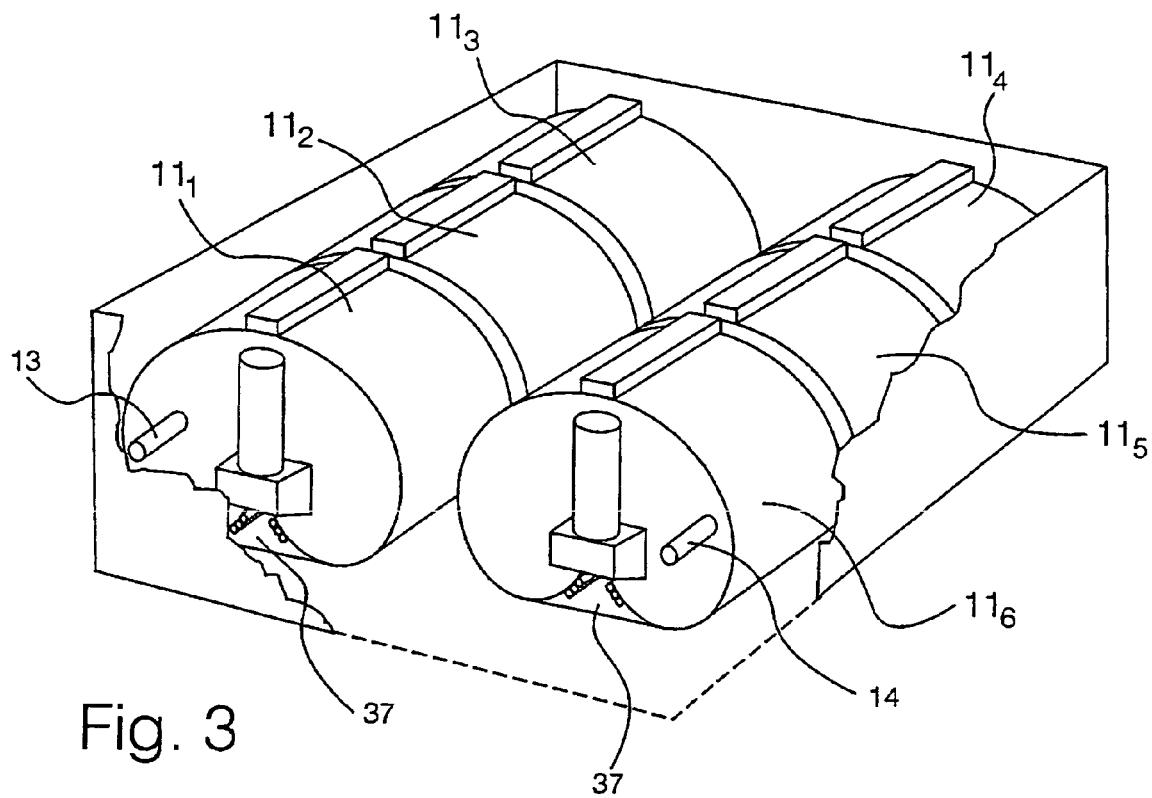
FIG. 3 is a schematic perspective view of an array of vessels forming a treatment system formed as an embodiment of the present invention.
Figure 4:
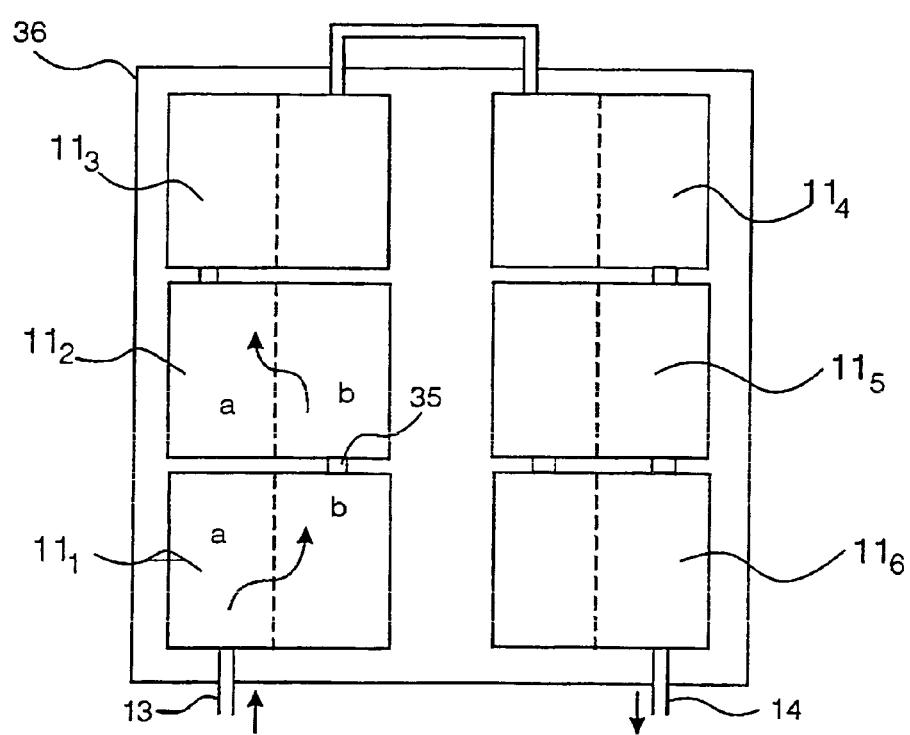
FIG. 4 is a plan view from above of the array of FIG. 3.

FIGS. 3 and 4 illustrate a system comprising a plurality of vessels (in this embodiment six are illustrated although the array may comprise 4, 8 or a larger number of vessels. Each vessel 11 in the array has been identified with an appropriate suffix $_1$ through $_6$ to identify its position in the sequence. As can be seen in FIG. 4 each vessel 11 is connected to the next vessel in the sequence on alternate sides a or b such that the inlet duct 13 to vessel $11_1$ opens into the left hand region a and the intercommunicating ducts 35 leading from region b of vessel $11_1$ opens into region b of vessel $11_2$.

The circulating flow within each side lobe of each vessel results, as described above, in a flow path comprising a spiral helix, which is represented by the curved arrow in each vessel illustrated in FIG. 4, it being appreciated that each flow path is represented only schematically and that no particle actually follows the path of the arrow but rather the more convoluted, extended path described in relation to FIGS. 1 and 2.

The vessels 11 are all contained within a bath or lagoon 36 (shown schematically) which is filled with a liquid to the same level as the process fluid in the tanks to equalise the pressures across the tank wall making it possible to use relatively thin sheet material, typically plastics, to contain the process fluid without requiring extremely high mechanical strength. The lagoon 36 may be formed as a pit for this reason.

Beneath the central cusp part of each vessel 11 is a heat exchanger 37 fed with heat exchange fluid as will be described in more detail below. The application of heat at this part of the vessel encourages convection currents which reinforce, and may even replace the forced circulation generated by the introduction of gas bubbles at the cusp.

In use of the apparatus described in relation to FIGS. 3 and 4, particularly in relation to a process fluid comprising a slurry of organic waste material, aerobic or anaerobic breakdown of the organic animal and/or plant materials takes place giving rise to simple substances. These may include a high proportion of gaseous and soluble products. The gaseous products, which in particular may include methane, are drawn off from the manifold 38 (see FIGS. 1 and 2) at the top of each vessel 11, or rather from the top of each of those vessels 11 in which the gaseous products are produced.

Of course, gaseous products are not necessarily immediately produced as the process taking place in the first vessel or chamber after introduction may comprise no more than preliminary aeration, with air being bubbled in as the circulation-driving medium. Only excess gas from this process is drawn from the first manifold. Thereafter, an anaerobic digestion process may take place which involves the cleaving, by extracellular enzymes, of polysaccharides, lipids and proteins, which are broken down to form sugars, fatty acids and glycerol. This initial part of the breakdown process, which for example takes place in vessel $11_2$, does not immediately give rise to gaseous products either. The preliminarily treated process fluid then passes into vessel $11_3$ and the process continues with the onset of fermentation by various organisms resulting in products which may include acetate, butyrate, ethanol, lactate, propionate and succinate together with carbon monoxide and hydrogen. These processes are very complex and this outline is intended only as an indication of some of the processes at work. The carbon monoxide and hydrogen are connected by bacteriological metabolisation to acetate by some of the bacteria present, whilst other bacteria may convert the carbon monoxide and hydrogen to methane.

The other vessels $11_4$, $11_5$ etc may be colonised by different bacteria due to the different conditions existing or set up in these vessels, such as temperature, pressure, flow rate etc. These bacteria may for example metabolise ethanol, lactate and other products of the initial fermentation resulting in acetate and hydrogen.

The temperatures at which the various bacteriological and/or other processes take place can be controlled by suitable means (not shown) including control of the heat exchangers 37.

The rate at which gases are introduced into the gas delivery pipes 19, 20 determines, together with the convection currents set up by the heat exchangers 37, the speed of circulation of the process fluid within the vessels and can be controlled independently (by means not illustrated). The residence time of the process fluid within the various vessels may also be controlled by means (not shown) such as bypass valves, shunt valves, subsidiary holding vessels, shut off valves, feedback or recirculation loops and the like. The choice of gas to be introduced as the circulation-driving gas through the duct 19, 20 may be air, for example in the first and last of the vessels $11_1$ and $11_6$ whereas methane may be introduced into the intermediate vessels $11_2$, $11_5$ and an inert gas into vessels $11_3$, $11_4$. The methane may of course be that generated by the digestion process itself. This may be recycled directly or drawn from storage containers.

The resulting digested slurry output from the last vessels $11_6$ in the series can then be passed to a separator where the solids are separated from the liquids to yield an odourless fertiliser rich in nutrients and a liquid which may also be used as a fertiliser (depending on the process fluid in question and the precise treatment process) or may be discharged perhaps after further final purification treatment.

In an alternative embodiment (not illustrated) the extraction of unwanted solids from the vessels as described in relation of FIG. 5, may incorporate the use of a pump in place of the auger 30 in the column 29, pumping a "plug" of water along the ducts to the outlet 31, or a gas lift system, especially one using air, may be employed.

Figure 6:
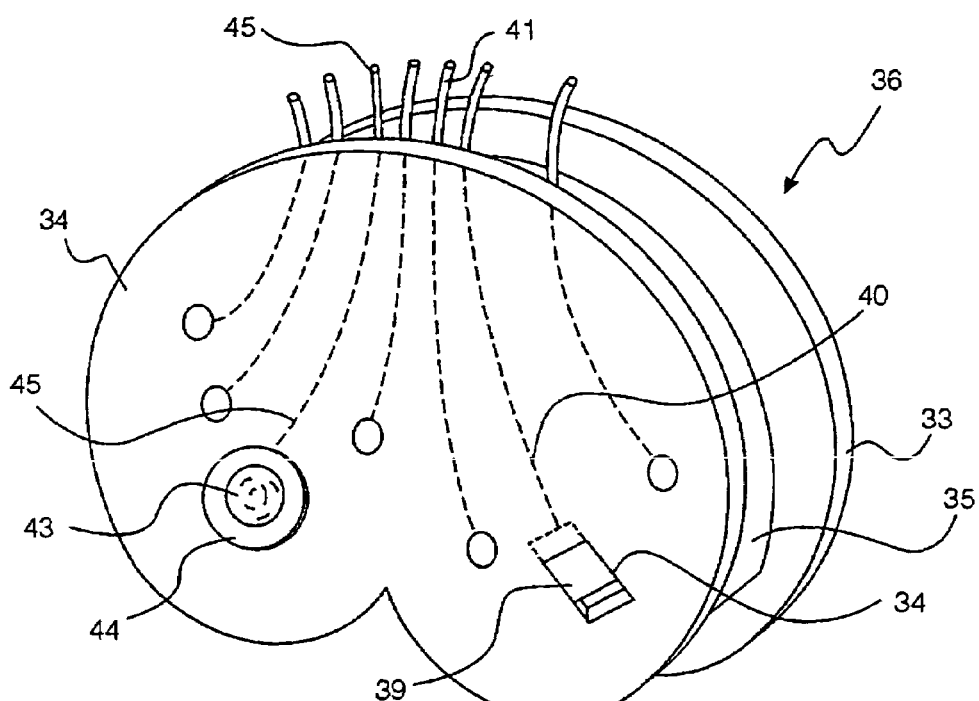
FIG. 6 is a schematic perspective view of a partition between two adjacent tanks.

FIG. 6 illustrates the form of a double-skin partition which may separate adjacent tanks in a multiple tank system such as that shown in FIG. 3. A peripheral bounding wall 35 separates two planar end walls 34, 33 to define an interior chamber. This allows one of the two end walls 34, 35 to comprise or include a semi-permeable membrane to permit the removal from the process fluid of constituents such as salt, heavy metals or other compounds. The location of the outlet 32 or transfer passage from one chamber to the next at a central point as illustrated in FIG. 6 plays its part in ensuring that the semi-permeable membrane remains clean due to the slight scouring action of the circulatory process fluid in contact with the semi-permeable membrane as it passes through the partition 36 from one chamber to the next.

This opening 32, as shown in FIG. 6, may be adjustable in size by for example the provision of an obturator plate 39 connected by a cable to a control handle 41 at the upper part of the partition, projecting above the top of the tank. By acting on the handle 41 a cable 40 is urged along its length one way or the other to vary the position of the obturator plate 39 and thus the flow cross section of the opening 32.

Between the two end plates there are also provided an array of sensors, including a microphone used as described above to detect the rate of circulating flow by the noise generated thereby. A safety pressure valve 42 is also located in the end walls, in the form of a ball 43 in a correspondingly shaped opening 44 into which it can be drawn by applying tension to a cable 45 leading out at the top of the tank adjacent the valve-opening handle 41. If a pressure differential greater than a predetermined threshold arises across the partition 36 the ball 43 is pushed out of the socket 44 to allow fluid to flow between the adjacent chambers and equalise the pressure in them or at least reduce the pressure differential. The ball 43 can be repositioned simply by applying tension to the cable 45 to cause the ball to be drawn back into the socket 44. A similar safety valve, but with a frangible outer plate (not shown) is provided at the end walls of the row of tanks which communicate with the lagoon.

Figure 7:
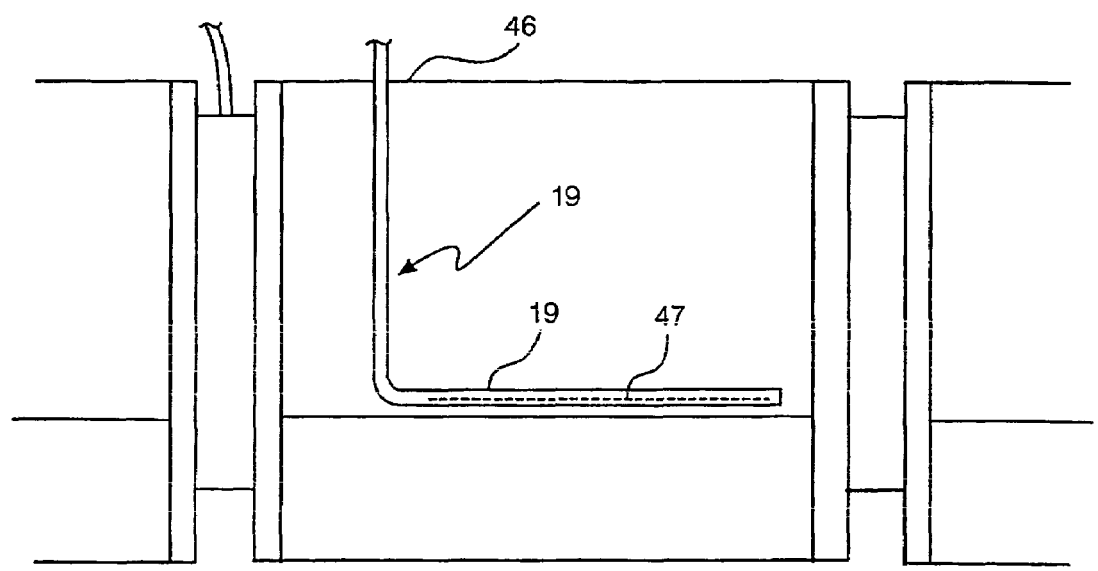
FIG. 7 is an axial sectional view of a tank structure incorporating the double-skin partition illustrated in FIG. 6.
Figure 8:
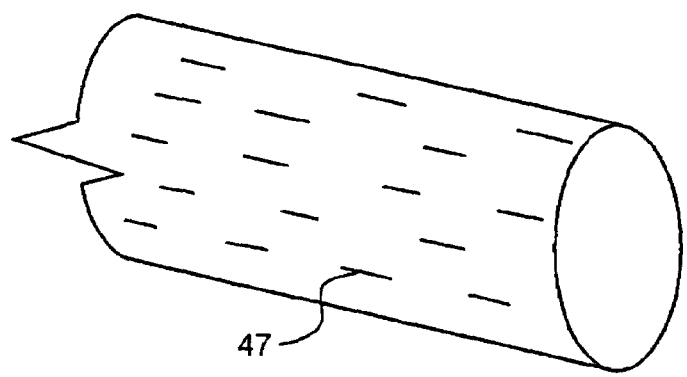
FIG. 8 is a schematic view of a gas delivery tube having slit-like exit openings.

FIGS. 7 and 8 illustrate the form of the gas delivery tube such as 19, 20 for use in an embodiment such as that illustrated where adjacent tanks are separated by double-skinned partitions as shown in FIG. 7. Here the delivery tube 19 is shown. It has a generally L-shape configuration to allow for removal through an upper opening 46 in the top of the tank. The horizontal limb 19$h$ has a plurality of slit-like openings 47 around its periphery. The material of the tube is slightly elastic so that the slits 47 open by the slight expansion of the tube when gas is delivered to it under a slight pressure. The openings 47 thus act as valves preventing any return flow of gas or fluid into the interior of the gas delivery tube even when no gas is delivered thereto.

Figure 9:
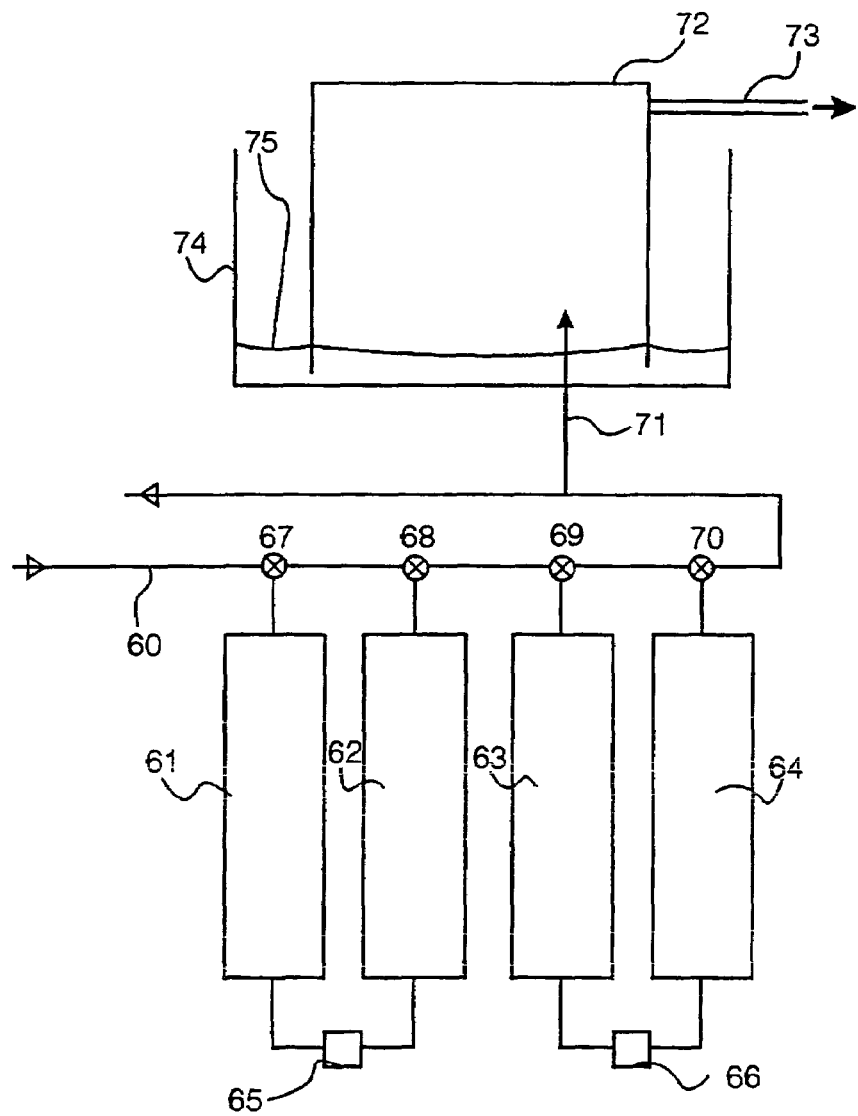
FIG. 9 is a schematic view of a gas pumping system for drawing off gas from the system.

FIG. 9 is a schematic diagram illustrating a pumping system for compressing the gas generated within the chambers, to which pipe 60 is connected. The pumping system comprises a number (in this case 4) of vertical hollow columns 61, 62, 63, 64 each partially filled with water and connected together in pairs by pumps 65, 66 at their lower ends. At their upper ends the hollow columns 61–64 are connected by valves 67, 68, 69, 70 to the pipe 60 and valve 70 is connected to a delivery pipe 71 leading to gas collection vessel 72 from which a compressed gas delivery outlet 73 leads onto a gas store (not shown).

The collection vessel 72 is in the form of an inverted "gasometer" configuration, the rim of which enters a liquid bath 75 in an upwardly open container 74.

In operation the valves 67–70 are controlled by a control circuit (not shown) to open and close selectively whereby to allow gas to enter from the pipe 60 into one or more of the hollow columns 61–64. When the column is full the appropriate valve is closed and water is pumped by the pump 65 or 66 from the companion tube into the gas-collection tube thereby compressing the gas therein. The valves 67–70 are then opened and/or closed as appropriate to form a path for the compressed gas into the gas collection vessel 72 from where it can be drawn off via the outlet 73 as required for further processing.

What is claimed is:

1. A treatment system for a process fluid, comprising a plurality of chambers interconnected with one another in sequence such that a process fluid can pass through them, and means for introducing a gas into at least one of the said chambers to form bubbles which act to drive circulation of the process fluid within the chamber as the bubbles rise within the process fluid, characterised in that at least one chamber having means for introducing a gas to form bubbles is provided with a heater which, in operation, creates convection currents in the process fluid resident in the said at least one chamber so as to reinforce the circulation of the process fluid driven by the bubbles of gas introduced into the chamber by the said gas introduction means.

2. A treatment system according to claim 1, characterised in that there are provided means for varying process parameters within selected chambers including temperature, pressure, circulation rate, residence time and the constitution of the atmosphere within a chamber.

3. A treatment system according to claim 1, characterised in that there are provided means for directing gas generated in one chamber as a result of the processes taking place therein selectively to the same and/or another chamber whereby to drive the circulation in that or the said other chamber.

4. A treatment system according to claim 1, characterised in that there are provided means for introducing air into the first and/or last chambers in the sequence whereby to effect aeration of the process fluid therein.

5. A treatment system according to claim 1, characterised in that there are provided temporary storage chambers or vessels between each said chamber of the system, and means for selectively directing process fluid from each chamber to the associated said storage chamber or vessel whereby to vary the residence time of the process fluid in a selected process chamber without discontinuing a continuous supply of process fluid to a first of the process chambers in the sequence.

6. A treatment system according to claim 1, characterised in that the chambers are formed as vessels connected together in sequence and arranged in two rows with a connecting duct at one end of each row and an inlet and an outlet from the system at opposite ends of respective rows.

7. A treatment system according to claim 1, characterised in that each chamber has associated means for removal of dense particles therefrom without interruption to the gas-tight sealing of the chamber.

8. A treatment system according to claim 1, characterised in that at least one chamber has an outlet the flow cross section of which is variable whereby to vary the overall rate of flow of process fluid through that chamber.

9. A treatment system according to claim 1, characterised in that each chamber comprises a containment vessel substantially entirely immersed in a bath or lagoon of liquid whereby to allow the pressure within the vessel to be substantially balanced by the pressure outside the vessel when it is filled with a process fluid.

10. A treatment system according to claim 1, characterised in that the shape of the chambers is such that the process fluid travels along the length of the chamber from one end to the other between inlet and outlet, in that the circulation path of the process fluid is transverse the length of the chamber, and in that the outlet from at least one of the chambers is located in an end wall of the chamber approximately centrally with respect to the circulating path of the process fluid in that part of the chamber so that relatively larger or denser particles of solid material entrained by the process fluid are effectively filtered out from the fluid exiting the chamber due to the vortex formed by the acceleration of the process fluid as it approaches the centrally located outlet.

11. A treatment system according to claim 1, characterised in that the means for introducing gas into a chamber includes an elongate gas delivery tube having a plurality of axially extending slits therein, the elasticity of the tube allowing the slits to act as individual unidirectional valves to allow the escape of gas from the tube but not the return flow even in the presence of a pressure differential between the inside and the outside of the tube.

12. A treatment system according to claim 1, characterised in that gas generated in a chamber is passed to a tube pumping system in which the gas pressure in a tube is varied by varying the liquid level therein and the liquid acts to seal the outlet from the tube.

13. A treatment system according to claim 1, in which the heater is arranged to apply heat to an exterior wall of the chamber.

14. A treatment system according to claim 1, in which the heater is in contact with an exterior wall of the chamber.

15. A treatment system according to claim 1, in which the heater comprises a heat exchanger.

16. Apparatus for processing fluids, comprising a chamber and means for introducing a gas into the chamber to form bubbles which act to drive circulation of the fluid within the chamber as the bubbles rise within the fluid, wherein the chamber is provided with a heater which, in operation, creates convection currents in the fluid so as to reinforce the circulation of the fluid driven by the bubbles.

17. Apparatus according to claim 16, in which the heater is arranged to apply heat to an exterior wall of the chamber.

18. Apparatus according to claim 16, in which the heater is in contact with an exterior wall of the chamber.

19. Apparatus according to claim 16, in which the heater comprises a heat exchanger.

20. Apparatus according to claim 16, in which the chamber has a generally cardioid cross-sectional shape and the heater is arranged to apply heat to the wall of the chamber at or in the vicinity of the cusp of the cardioid.

21. A treatment system for a process fluid, comprising a plurality of chambers interconnected with one another in sequence such that a process fluid can pass through them, and means for introducing a gas into at least one of the said chambers to form bubbles which act to drive circulation of the process fluid within the chamber as the bubbles rise within the process fluid, characterised in that at least one chamber having means for introducing a gas to form bubbles is provided with a heater which, in operation, creates convection currents in the process fluid resident in the said at least one chamber so as to reinforce the circulation of the process fluid driven by the bubbles of gas introduced into the chamber by the said gas introduction means wherein said heater comprises a heat exchanger not in wetted contact with the process fluid and in thermal contact with a wall of said chamber.

22. A treatment system according to claim 21, characterised in that the chambers each have a generally cardioid cross sectional shape and the heater is arranged to apply heat to the wall of the chamber at or in the vicinity of the cusp of the cardioid.

* * * * *